United States Patent [19]

Ichiba et al.

[11] Patent Number: 5,514,705

[45] Date of Patent: May 7, 1996

[54] EPIDIOXYMANADIC ACIDS A AND B

[75] Inventors: Toshio Ichiba, Nagoya, Japan; Paul J. Scheuer, Honolulu, Hi.; Dolores G. Gravalos, Madrid, Spain

[73] Assignee: PharmaMar, S.A., Madrid, Spain

[21] Appl. No.: 303,049

[22] Filed: Sep. 7, 1994

[51] Int. Cl.⁶ .................. A61K 31/35; C07D 319/02
[52] U.S. Cl. ............................ 514/452; 549/357
[58] Field of Search .............. 549/357; 514/452

[56] References Cited

U.S. PATENT DOCUMENTS 4,731,377  3/1988  Higa et al. ............... 514/452

OTHER PUBLICATIONS

Kobayashi et al., CA: 121: 35137 (1993)–Abstract of Chem. Pharm. Bull. (1993), 41(7), 1324–6.

*Primary Examiner*—Nicky Chan
*Attorney, Agent, or Firm*—Ernest V. Linek

[57] ABSTRACT

The present invention is directed to two novel compounds isolated from a Pacific sponge, Plakortis (Homosclerophorida, Plakinidae) which are designated herein as epidioxymanadic acids A and B. These two compounds have been obtained by a bioassay-guided (i.e., antibiotic activity) isolation procedure, involving solvent partition and chromatography on Sephadex LH-20, cyano, and C-18 columns, from extracts of sponge.

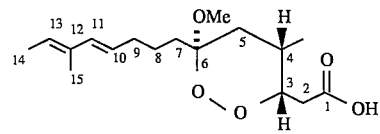

Epidioxymanadic Acid A

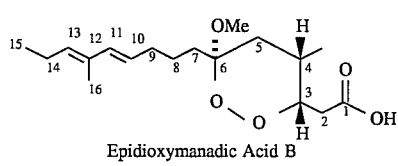

Epidioxymanadic Acid B

6 Claims, 1 Drawing Sheet

Pacific sponge, *Plakortis sp.* (dry weight 130 g)

Extracted with EtOH

↓

| | |
|---|---|
| ↓ | ↓ |
| MeOH | CH$_2$Cl$_2$/EtOH 5:1 solubles (9.8 g) |

↓

Part of the extract (1.0 g)

↓

HSCCC with
EtOAc/heptane/MeOH/H$_2$O
(7:4:4:3)

↓

HSCCC with
heptane/MeCN/CH$_2$Cl$_2$
(10:7:3)

↓

| ↓ | ↓ |
|---|---|
| Epidioxymanadic acid A (1, 46 mg) | Epidioxymanadic acid B (2, 5 mg) |

FIGURE

EPIDIOXYMANADIC ACIDS A AND B

SUMMARY OF THE INVENTION

The present invention is directed to two novel compounds isolated from a Pacific sponge, Plakortis (Homosclerophorida, Plakinidae) which are designated herein as epidioxymanadic acids A and B. These two compounds have been obtained by a bioassay-guided isolation procedure (i.e., antibiotic activity), involving solvent partition and high speed countercurrent chromatography (HSCCC) of extracts of the Pacific sponge.

The compounds of the present invention are carboxylic acids. Thus, it is believed that pharmaceutically acceptable salts may be prepared from said compounds. The term "pharmaceutically acceptable salts" refers to salts prepared from pharmaceutically acceptable non-toxic bases including inorganic bases and organic bases. Salts derived from inorganic bases include sodium, potassium, lithium, ammonium, calcium, magnesium, ferrous, zinc, copper, manganous, aluminum, ferric, manganic, and the like. Particularly preferred are the ammonium, potassium, sodium, calcium and magnesium salts. Salts derived from pharmaceutically acceptable organic non-toxic bases include salts of primary, secondary, and tertiary amines, substituted amines including naturally occurring substituted amines, cyclic amines and basic anion exchange resins, such as isopropylamine, trimethylamine, diethylamine, triethylamine, tripropylamine, ethanolamine, 2-dimethylaminoethanol, 2,2-diethylaminoethanol, tromethamine, lysine, arginine, histidine, caffeine, procaine, hydrabamine, methylglucamine, theobromine, purines, piperazine, piperidine, N-ethylpiperidine, polyamine resins and the like. Particularly preferred organic non-toxic bases are isopropylamine, diethylamine, ethanolamine, piperidine, tromethamine, choline and caffeine.

As discussed in greater detail below, the compounds of the present invention have been found to possess antitumor activity both in vitro and in vivo, and as such it is believed that these cytotoxic compounds will be useful as antitumor compounds in animals and preferably in humans. When being used as cytotoxic or antitumor agents, the compounds of the present invention can be prepared and administered in various dosage forms, especially parenteral dosage forms. It will be clear to those having ordinary skill in this art that the dosage forms may comprise as the active ingredient, one or more of the compounds of the present invention. The skilled artisan will likewise recognize that the dosages and routes of administration will vary according to the needs of the patient and the specific activity of the active ingredient(s). The determination of these parameters is within the ordinary skill of the practicing physician.

Also, as discussed above, the bioassay guided isolation scheme relied upon by the present inventors utilized the antibiotic activity of the compounds of the present invention as a guide for their separation from the sponge. As such, the compounds of the present invention also possess antibiotic activity, and will be useful as antibacterial agents, particularly in animals and preferably in humans. When being used as antibacterial agents, the compounds of the present invention can be prepared and administered in various dosage forms, especially parenteral dosage forms. It will be clear to those having ordinary skill in this art that the dosage forms may comprise as the active ingredient, one or more of the compounds of the present invention. The skilled artisan will likewise recognize that the dosages and routes of administration will vary according to the needs of the patient and the specific activity of the active ingredient(s). The determination of these parameters is within the ordinary skill of the practicing physician.

BRIEF DESCRIPTION OF THE DRAWING

The Figure illustrates one preferred isolation scheme useful for obtaining the compounds of the present invention.

DETAILED DESCRIPTION OF THE PREFERRED EMBODIMENTS

I. Collection and Identification.

The sponge source of the compounds of the present invention was collected in the Pacific Ocean at a depth of −10 to −20 m from a rocky surface off the coast of Manado, Sulawesi, Indonesia (1°29'N, 124°51'E) on Oct. 1, 1992. This Pacific sponge formed a thick encrustation with a smooth surface and liver-like texture, and was light tan colored both in life and in EtOH preservative. The sample contained randomly and densely distributed contriangulate diactines 90–100 μm in length.

A sample of this Pacific sponge was compared to Plakortis lita de Laubenfels from the West Central Pacific and Plakortis simplex sensu Topsent (1897) from Amboyne, Moluccas, Indonesia, but both possess triactines. *P. lita* and *P. simplex* also differ considerably in coloration from the sample of the present invention; lita being dark reddish brown with a red interior and simplex being a dull dark blue with a yellowish interior. The sponge sample of the present invention has thus been designated as a previously undescribed species of Plakortis (Homosclerophorida, Plakinidae). The taxonomical identification was carried out by Dr. Michele Kelly-Borges, HBOL.

II. Isolation

The Figure describes the general isolation procedures employed to isolate the compounds of the present invention from the Pacific sponge. As illustrated, the sponge (130 g, dry) was freeze-dried, and then extracted with EtOH (3×1.5 L). The EtOH extract was concentrated to dryness. $CH_3Cl_2$/EtOH 5:1 (100 mL) was added to the residual solid of the EtOH extract, then non-polar substances were triturated to yield 9.8 g of a brown oil.

A portion (1.0 g) of the non-polar extract was separated by bioassay-guided (Gram-positive bacteria) fractionation by high speed countercurrent chromatography (HSCCC), first with a solvent system of $EtOAc/heptane/MeOH/H_2O$ 7:4:4:3 (upper mobile phase), then $heptane/MeCN/CH_2Cl_2$ 10:7:3 (lower mobile phase), yielding both epidioxymanadic acid A (1, 46 mg) and epidioxymanadic acid B (2, 5 mg), as colorless oils. As described above, in addition to the antitumor activity discussed below, the compounds of the present invention are also believed to be useful as antibacterial agents, particularly against Gram-positive bacteria.

III. Physical Data

As isolated, the compounds epidioxymanadic acid A and epidioxymanadic acid B, are obtained in substantially pure form. The following physical and chemical characteristics were determined on the purified compounds:

A. Epidioxymanadic acid A (1): $[\alpha]_D^{18}$ +83.9° (MeOH, c 43.8); UV (MeOH) $\lambda_{max}$ 232 nm ($\epsilon$30500); IR ($CCl_4$, NaCl cell) $v_{max}$ 3500–2400 (broad), 2950, 2930, 1710, 1430, 1300, 1270, 1070, 960 cm$^{-1}$; $^1$H NMR (300 MHz, $CDCl_3$) shown in Table 1; $^{13}$C NMR (75 MHz, $CDCl_3$) shown in Table 1; EIMS m/z 264 (M$^+$-MeOH-O), 236 HREIMS observed m/z 264.1738, calcd 264.1726 for $C_{16}H_{24}O_3$ (M$^+$-

MeOH-O) (Δ1.2 mmu); HRFAB m/z 295.1909, calcd 295.1910 for $C_{17}H_{27}O_4$ ($M^+$ +H -MeOH) (Δ0.1 mmu).

B. Epidioxymanadic acid B (2); $[\alpha]^{D18}$+130.3° (MeOH, c 4.0); UV (MeOH) $\lambda_{max}$ 234 nm ($\epsilon$13400); IR ($CCl_4$, NaCl cell) $v_{max}$ 3500–2400 (broad), 2950, 2920, 1710, 1430, 1300, 1060, 960 $cm^{-1}$; $^1H$ NMR (300 MHz, $CDCl_3$) shown in Table 1: $^{13}C$ (75 MHz, $CDCl_3$) shown in Table 1; EIMS m/z 264, 248.

The following table provides $^{13}C$ and $^1H$ NMR data for these two compounds:

TABLE I

NMR Data ($CDCl_3$) of Epidioxymanadic Acids A (1) and B (2)

| Carbon | Epidioxymanadic acid A (1) $^{13}C$ | $^1H$ | Epidioxymanadic acid B (2) $^{13}C$ | $^1H$ |
|---|---|---|---|---|
| 1 | 176.3 | | 175.2 | |
| 2 | 35.2 | 2.51 dd J = 16.5, 8.9 Hz | 35.0 | 2.54 dd J = 16.2, 8.7 Hz |
|   |      | 2.37 dd J = 16.5, 4.9 Hz |      | 2.40 dd J = 16.2, 4.8 Hz |
| 3 | 78.9 | 4.64 ddd J = 8, 9, 4.8, 2.7 Hz | 78.9 | 4.65 ddd J = 8.7, 4.8, 2.7 Hz |
| 4 | 28.5 | 1.90 m | 28.7 | 1.92 m |
| 5 | 36.9 | 1.82 dd J = 13.8, 5.4 Hz | 37.0 | 1.85 dd J = 13.5, 5.4 Hz |
|   |      | 1.74 dd J = 13.8, 3.0 Hz |      | 1.76 dd J = 13.5, 2.7 Hz |
| 6 | 103.6 | | 103.6 | |
| 7 | 32.4 | 1.30 m | 32.4 | 1.62 m |
|   |      | 1.62 m |      | 1.35 m |
| 8 | 23.1 | 1.41 m | 23.1 | 1.43 m |
| 9 | 32.7 | 2.07 q J = 6.9 Hz | 32.8 | 2.08 q J = 7.2 Hz |
| 10 | 126.0 | 5.47 dt J = 15.6, 6.9 Hz | 126.3 | 5.50 dt J = 15.6, 7.2 Hz |
| 11 | 135.5 | 6.04 d J = 15.6 Hz | 135.6 | 6.05 d J = 15.6 Hz |
| 12 | 134.2 | | 132.8 | |
| 13 | 124.9 | 5.45 q J = 6.9 Hz | 132.8 | 5.38 t J = 7.4 Hz |
| 14 | 12.0 | 1.68 d J = 6.9 Hz | 21.4 | 2.11 quint J = 7.4 Hz |
| 15 | 13.7 | 1.69 s | 14.1 | 0.96 t J = 7.4 Hz |
| 16 | 14.2 | 1.09 d J = 7.2 Hz | 12.3 | 1.70 s |
| 17 | 48.0 | 3.21 s | 14.2 | 1.11 d J = 7.2 Hz |
| 18 | | | 48.2 | 3.23 s |

IV. Molecular Structures of the Acids

Based on the above data and some chemical transformations, the molecular structures of the two acids have been determined to be as follows:

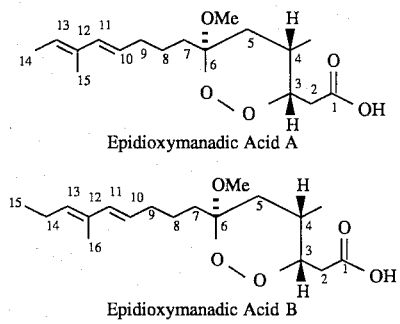

Epidioxymanadic Acid A

Epidioxymanadic Acid B

V. Biological Activities

In addition to the Gram-positive antibacterial effect exhibited by the compounds of the present invention (in vitro) and utilized in connection with the isolation process for the present compounds, the compounds of the present invention exhibit comparable and significant cytotoxicity against the P388, A549, HT29 and MEL-28 cell lines in culture. Table 2 demonstrates this, showing $IC_{50}$ values ranging from about 0.5 to 5 µg/ml. Based upon these data, it is believed that the compounds disclosed herein will be useful as antitumor compounds, particularly against the following tumor cell types; leukemia (P388), human lung carcinoma (A549), human colon carcinoma (HT-29), human melanoma (MEL-28).

TABLE 2

| COMPOUND | $IC_{50}$ (µg/ml) P388 | A549 | HT29 | MEL-28 |
|---|---|---|---|---|
| Epidioxymanadic A | 0.5 | 1 | 2 | 5 |

TABLE 2-continued

| COMPOUND | $IC_{50}$ (µg/ml) P388 | A549 | HT29 | MEL-28 |
|---|---|---|---|---|
| Epidioxymanadic B | 0.5 | 1 | 2 | 2.5 |

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. The compound Epidioxymanadic Acid A, in substantially pure form, and having the following structure:

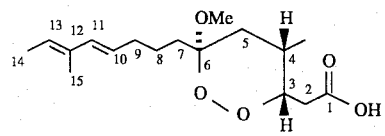

and pharmaceutically acceptable salts thereof.

2. The compound Epidioxymanadic Acid B, in substantially pure form, and having the following structure:

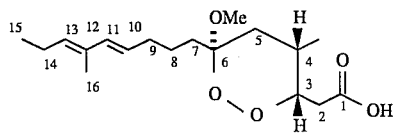

and pharmaceutically acceptable salts thereof.

3. A method of treating Gram-positive bacterial infections in mammals comprising administering to a patient in need of such treatment, an effective antibacterial amount of the compound Epidioxymanadic Acid A, or a pharmaceutically acceptable salt thereof, in an optional carrier, diluent or excipient.

4. A method of treating Gram-positive bacterial infections in mammals comprising administering to a patient in need of such treatment, an effective antibacterial amount of the compound Epidioxymanadic Acid B, or a pharmaceutically acceptable salt thereof, in an optional carrier, diluent or excipient.

5. A method of treating mammalian tumors selected from the group consisting of leukemia, lung carcinoma, colon carcinoma and melanoma, comprising administering to a patient in need of such treatment, an effective antitumoral amount, of the compound Epidioxymanadic Acid A, or a pharmaceutically acceptable salt thereof, in an optional carrier, diluent or excipient.

6. A method of treating mammalian tumors selected from the group consisting of leukemia, lung carcinoma, colon carcinoma and melanoma, comprising administering to a patient in need of such treatment, an effective antitumoral amount of the compound Epidioxymanadic Acid B, or a pharmaceutically acceptable salt thereof, in an optional carrier, diluent or excipient.

* * * * *